(12) United States Patent
Buckman

(10) Patent No.: US 7,178,932 B1
(45) Date of Patent: Feb. 20, 2007

(54) WELDING HELMET

(76) Inventor: Michael Allen Buckman, P.O. Box 792, Pablo, MT (US) 59855

( * ) Notice: Subject to any disclaimer, the term of this patent is extended or adjusted under 35 U.S.C. 154(b) by 0 days.

(21) Appl. No.: 11/324,913

(22) Filed: Jan. 4, 2006

(51) Int. Cl.
*F21V 21/084* (2006.01)
(52) U.S. Cl. ............ 362/105; 362/106; 362/373; 219/147; 2/8.6
(58) Field of Classification Search .......... 362/105, 362/106, 373; 219/147; 2/8.2, 8.6
See application file for complete search history.

(56) References Cited

U.S. PATENT DOCUMENTS

| 3,238,535 | A | * | 3/1966 | Hugh | 2/8.1 |
| 3,535,707 | A | * | 10/1970 | Greenlee | 128/200.27 |
| 3,649,964 | A | * | 3/1972 | Schoelz et al. | 128/205.25 |
| 4,309,774 | A | * | 1/1982 | Guzowski | 2/8.6 |
| 5,029,342 | A | * | 7/1991 | Stein et al. | 2/8.6 |
| 5,031,237 | A | * | 7/1991 | Honrud | 2/8.6 |
| 5,123,114 | A | * | 6/1992 | Desanti | 2/8.6 |
| 5,561,855 | A | * | 10/1996 | McFall | 2/8.6 |
| 5,896,579 | A | * | 4/1999 | Johnson et al. | 2/8.6 |
| 6,340,234 | B1 | * | 1/2002 | Brown, Jr. | 362/105 |
| 2005/0077278 | A1 | * | 4/2005 | Steinemann | 219/147 |

FOREIGN PATENT DOCUMENTS

| CA | 2184929 | * | 3/1998 |
| GB | 1511303 | * | 5/1978 |
| WO | WO 81/02514 | * | 9/1981 |

* cited by examiner

*Primary Examiner*—Stephen F. Husar
(74) *Attorney, Agent, or Firm*—Michael I Kroll

(57) ABSTRACT

Apparatus 10 discloses an improved welders helmet having a replaceable lens 16 thereon incorporating an electrically driven fan 14 which receives filtered air through a plurality of air ducts 24 having a filter 22 thereon. A receptacle 20 for containing a battery is disposed on the helmet along with photovoltaic elements 32 for recharging the batteries from the flash of the weld. Lights 30 are also disposed on the helmet.

11 Claims, 9 Drawing Sheets

WELDING HELMET

BACKGROUND OF THE INVENTION

1. Field of the Invention

The present invention relates generally to protective devices and, more specifically, to an improved welders helmet incorporating means for directing airflow both internally and externally, means for filtering noxious elements from air for breathing; means for directing air within the helmet, especially across the visor; means for energizing fans incorporated into the helmet; means for recharging the power supply and selectively illuminable elements for workpiece sight enhancement.

2. Description of the Prior Art

There are other helmet devices designed for protection. Typical of these is U.S. Pat. No. 3,238,535 issued to Richey on Mar. 8, 1966.

Another patent was issued to Greenlee on Oct. 27, 1970 as U.S. Pat. No. 3,535,707. Yet another U.S. Pat. No. 3,649,964 was issued to Schoelz on Mar. 21, 1972 and still yet another was issued on Jan. 12, 1982 to Guzowski as U.S. Pat. No. 4,309,774.

Another patent was issued to Stein, et al. on Jul. 9, 1991 as U.S. Pat. No. 5,029,342. Yet another U.S. Pat. No. 5,031,237 was issued to Honrud on Jul. 16, 1991. Another was issued to Desanti on Jun. 23, 1992 as U.S. Pat. No. 5,123,114 and still yet another was issued on Oct. 8, 1996 to McFall as U.S. Pat. No. 5,561,855.

Another patent was issued to Johnson, et al. on Apr. 27, 1999 as U.S. Pat. No. 5,896,579. Yet another U.K. Patent No. GB1511303 was issued to Kemira on May 17, 1978. Another was issued to Berg, et al. on Sep. 17, 1981 as International Patent Application No. WO81/02514 and still yet another was issued on Mar. 7, 1998 to Johnson as Canadian Patent No. CA2184929

U.S. Pat. No. 3,238,535

Inventor: Willie H. Richey

Issued: Mar. 8, 1966

In a welding hood having a protective front surface including a lens through which the hood user may view his work and rearwardly directed side and top surfaces formed integrally with the front surface, the improvement comprising: a transversely oriented cylindrical tube mounted across the hood side surfaces at a location adjacent the inner front surface and above the hood lens, said tube having axially open ends open respectively through apertures formed in the hood side surfaces; an electric motor mounted coaxially within said tube at the longitudinal center thereof, said motor having a driven shaft protruding axially outward at each end thereof; a pair of complementary fan blade units fixed to the motor shaft at the respective axial ends thereof, said blade units being each adapted to draw air axially toward the tube center when rotated by said motor; said tube being further provided with a lower aperture formed therethrough at the longitudinal center of the tube and directed downwardly adjacent the inside front surface of said hood; and light responsive electrical generating means mounted on the exterior of said hood and directed forwardly therefrom, said generating means being wired to said motor so as to operate said motor in response to light incident thereon U.S. Pat. No. 3,535,707

Inventor: Harry R. Greenlee

Issued: Oct. 27, 1970

A welding helmet or the like, comprising a face shielding mask, first means for mounting said mask onto an operator's head, an opening formed through said mask, said opening being so formed as to be generally forwardly directed with respect to said mask, an electrically driven motor, a fan assembly operatively connected to said motor so as to be rotatably driven thereby, and second means carried generally within said opening and operatively connected to said mask for carrying said motor and fan assembly, said second means being effective for positioning said fan assembly in any of a plurality of varying attitudes with respect to said mask in order to enable said fan assembly to direct a stream of air in a selected direction corresponding to a selected one of said plurality of attitudes.

U.S. Pat. No. 3,649,964

Inventor: Willy A. E. Schoelz

Issued: Mar. 21, 1972

Ventilating means for a welder's face mark employing a battery-operated blower secured on the mask. Air passageways are provided in the mask which lead from the blower to inlet openings interiorly of the mask for ventilating the area between the mask and the welder's face. Batteries for operating the blower are mounted on the head band, and in structure utilizing a mask which can be tipped up on the headband, switch means are employed between the face mask and the headband which activate the blower in the down position of the mask and deactivate the blower in the up position of the mask.

U.S. Pat. No. 4,309,774

Inventor: Chester D. Guzowski

Issued: Jan. 12, 1982

A ventilating helmet which takes the form of sheet material wall member which has mounted thereon an electrically operated fan which is adapted to move air to the interior of the helmet. The electrically operated fan is to be operated through the use of a light sensitive, electrical energy producing cell. This cell is to be directly exposed to the source of light energy.

U.S. Pat. No. 5,029,342

Inventor: Marc F. Stein, et al

Issued: Oct. 25, 1989

A welder's helmet including a panel of solar cells responsive to light generated by a welding operation to drive a fan incorporated in the helmet structure. The solar cells are mounted on the helmet above the viewing window and the fan is mounted in front of the mask below the viewing window. When a welding arc is struck, the light from the torch impinges on the solar panel and generates sufficient electricity to drive the fan. The fan forces air from the inside of the helmet outward through the front face in a velocity controlled stream carefully directed to prevent smoke and fumes from reaching the helmet, and to also blow the smoke away from the weld site in a particular manner so that visibility of the weld remains clear while not over-oxygenating the weld site. As air is exhausted from the inside of the helmet outward by the fan, fresh air is drawn in around the sides to replace that which is being exhausted to cool the welder and prevent ingestion of fumes and vapors. A photovoltaic power transmission circuit is provided to process electrical energy derived from light such as that produced by the arc of an arc welder during a welding operation.

U.S. Pat. No. 5,031,237

Inventor: Gregory S. Honrud

Issued: Jul. 16, 1991

The present invention comprises apparatus and methods of using a light sensitive switch, such as a photo-electric or photo-resistive cell, to actuate a battery powered electric motor which rotates a fan blade located within a housing near a facial area of a welding helmet. When exposed to a high intensity light, such as the light emitted during a welding process, the photoconductive cell actuates the battery powered motor. When activated, the motor rotates the fan blade which draws air away from the face of a wearer and passes such air through a filter into an air flow chamber, thereby, filtering the drawn air. The rotation of the fan blade then forces the filtered air toward the facial area of the wearer. A smoke block, which restricts the entrance of smoke or other contaminated vapors from entering the confines between the interior surface of the helmet and the face of the wearer, may be removably attached to the helmet.

U.S. Pat. No. 5,123,114

Inventor: Michael J. Desanti

Issued: Jun. 23, 1992

A ventilated welding mask is disclosed having a three chamber housing mounted thereon. A blower fan is positioned within a second medial chamber. On the rear wall of the second medial chamber, a nozzle is mounted. A conduit extends from this nozzle to an air flow manifold positioned with the welding mask.

U.S. Pat. No. 5,561,855

Inventor: Mike G. McFall

Issued: Oct. 8, 1996

A welder's helmet having a plurality of photovoltaic cell panels, responsive to light produced during welding operations, for driving a pair of fans secured to opposing side walls of a head protecting shell. The photovoltaic cell panels are angularly mounted to the shell beneath a viewing window provided therein so as to permit the head of the wearer to be turned away from the welding area without affecting fan output. During operation, each of the paired fans impels air through an opening in the shell into the interior space defined by the shell. An optional battery pack, electrically connected to the fan motors provides an electrical power back-up for energizing the fans in the event that insufficient light is available to the photovoltaic panels.

U.S. Pat. No. 5,896,579

Inventor: Bennett Johnson, et al.

Issued: Apr. 27, 1999

A welding helmet with an air circulating system that includes a welding hood, a head band assembly, and an air circulating system. The welding hood has an interior face receiving cavity defined by an interior helmet surface. The head band assembly being pivotally mounted to the welding helmet. The air circulating system including an air circulating assembly mounted to a top portion of the welding hood, a cooling water storage bottle attached to a back portion of the head band, a wick conduit connected between the air circulating assembly and the cooling water storage bottle, a detachable battery pack housing mountable to a front structure of the air cooling assembly, and a pivotally actuated air circulating assembly on/off switch mounted between the welding hood and the head band.

U.K. Patent Number GB1511303

Inventor: Kemira Oy

Issued: May 17, 1978

A tube with holes 4 for discharging air, closed at one end e.g. by squeezing and connectable at the other to a compressed-air hose, is used for noise suppression of air flow and direction of air flow in personal protective headgear. The tube reduces the noise level of discharging air. The tube also directs the air flow to prevent draughts and keep the front window or net of the headgear clean and dry. The straight or curved cylindrical aluminum tube is 5 to 20 mm diameter, 30 cm long and perforated by 50 round holes 4 whose diameters are from 0.7 mm. to 2 mm. Gauge pressures in the tube of 0.2 kgf/cm$^2$ and 1.2 kgf/cm$^3$ produce a free air flow of 60 L/min and 170 L/min respectively. A synthetic e.g. woven nylon ribbon is wound around the tube in one or more layers or a stocking is used. The tube is attached with hose-clips to the helmet.

International Patent Application Number WO81/02514

Inventor: Richard C. Berg, et al

Issued: Sep. 17, 1981

A powdered air respirator (10) designed to provide respiratory, eye and face protection and comprises a hardhat (11), a shell member (20) secured to the hardhat and spaced therefrom to form a generally dome-shaped passageway therebetween, air filtering means (30) in the passageway between the shell member and the hardhat, a face shield assembly (35) attached to and depending from the front of the shell member, a transparent face shield (60) in said face shield assembly, face sealing means (65) on the peripheral edge of said face shield assembly to seal against a user's face from temple to temple provided with air exits adjacent each temple and an air circulating means (70) located in the rear portion of the passageway between the shell member and the hardhat for directing a flow of air through the passageway, air filtering means, interior of the face shield assembly and out through the air exits.

Canadian Patent Number CA2184929

Inventor: Michael Johnson

Issued: Mar. 7, 1998

This is a device for protecting a persons head while working in a hazardous environment i.e. steel industry—welding, grinding or other places where there are hazards to health (lungs, eyes and ears) and a person needs face and head protection from flying particles which may harm an individual. This invention consists of a helmet with a face shield. The helmet also consists of two (2) air filters in which each has a fan to propel air into the helmet. The fans have a rechargeable battery pack for a power source. On the bottom of the helmet is provided a piece of nonflammable material, quite soft and flexible, to provide protection to the throat and neck area from foreign materials and ultraviolet rays. The helmet being made of materials designed to provide the same protection as a hard hat.

While these protective devices may be suitable for the purposes for which they were designed, they would not be as suitable for the purposes of the present invention, as hereinafter described.

SUMMARY OF THE PRESENT INVENTION

The present invention discloses an improved welders helmet incorporating means for directing airflow both internally and externally, means for filtering noxious elements from air for breathing; means for directing air within the helmet, especially across the visor; means for energizing fans incorporated into the helmet; means for recharging the power supply and selectively illuminable elements for workpiece sight enhancement.

A primary object of the present invention is to provide an improved welders helmet.

Another object of the present invention is to provide a welders helmet comprising a housing mountable to a user's head having a viewing port with strategically placed vents, fans, lighting, in electrical communication with a portable power source.

Yet another object of the present invention is to provide a welders helmet having filter elements for removing noxious particles from air prior to inhalation.

Still yet another object of the present invention is to provide a welder's helmet having fans for directing airflow to prevent introduction of noxious fumes.

Another object of the present invention is to provide a welders helmet incorporating airflow directionals to keep the wearer cooler and prevent condensation on the view port.

Yet another object of the present invention is to provide a welders helmet having lighting elements for selectively illuminating a workpiece.

Still yet another object of the present invention is to provide a welder's helmet having a portable power source in electrically communication with said helmet.

Another object of the present invention is to provide a welder's helmet having photovoltaic elements for recharging the power source.

Additional objects of the present invention will appear as the description proceeds.

The present invention overcomes the shortcomings of the prior art by providing an improved welders helmet incorporating means for directing airflow both internally and externally, means for filtering noxious elements from air for breathing; means for directing air within the helmet, especially across the visor; means for energizing fans incorporated into the helmet; means for recharging the power supply and selectively illuminable elements for workpiece sight enhancement.

The foregoing and other objects and advantages will appear from the description to follow. In the description reference is made to the accompanying drawings, which form a part hereof, and in which is shown by way of illustration specific embodiments in which the invention may be practiced. These embodiments will be described in sufficient detail to enable those skilled in the art to practice the invention, and it is to be understood that other embodiments may be utilized and that structural changes may be made without departing from the scope of the invention. In the accompanying drawings, like reference characters designate the same or similar parts throughout the several views.

The following detailed description is, therefore, not to be taken in a limiting sense, and the scope of the present invention is best defined by the appended claims.

BRIEF DESCRIPTION OF THE DRAWINGS

In order that the invention may be more fully understood, it will now be described, by way of example, with reference to the accompanying drawings in which.

LIST OF REFERENCE NUMERALS

Figure 1:
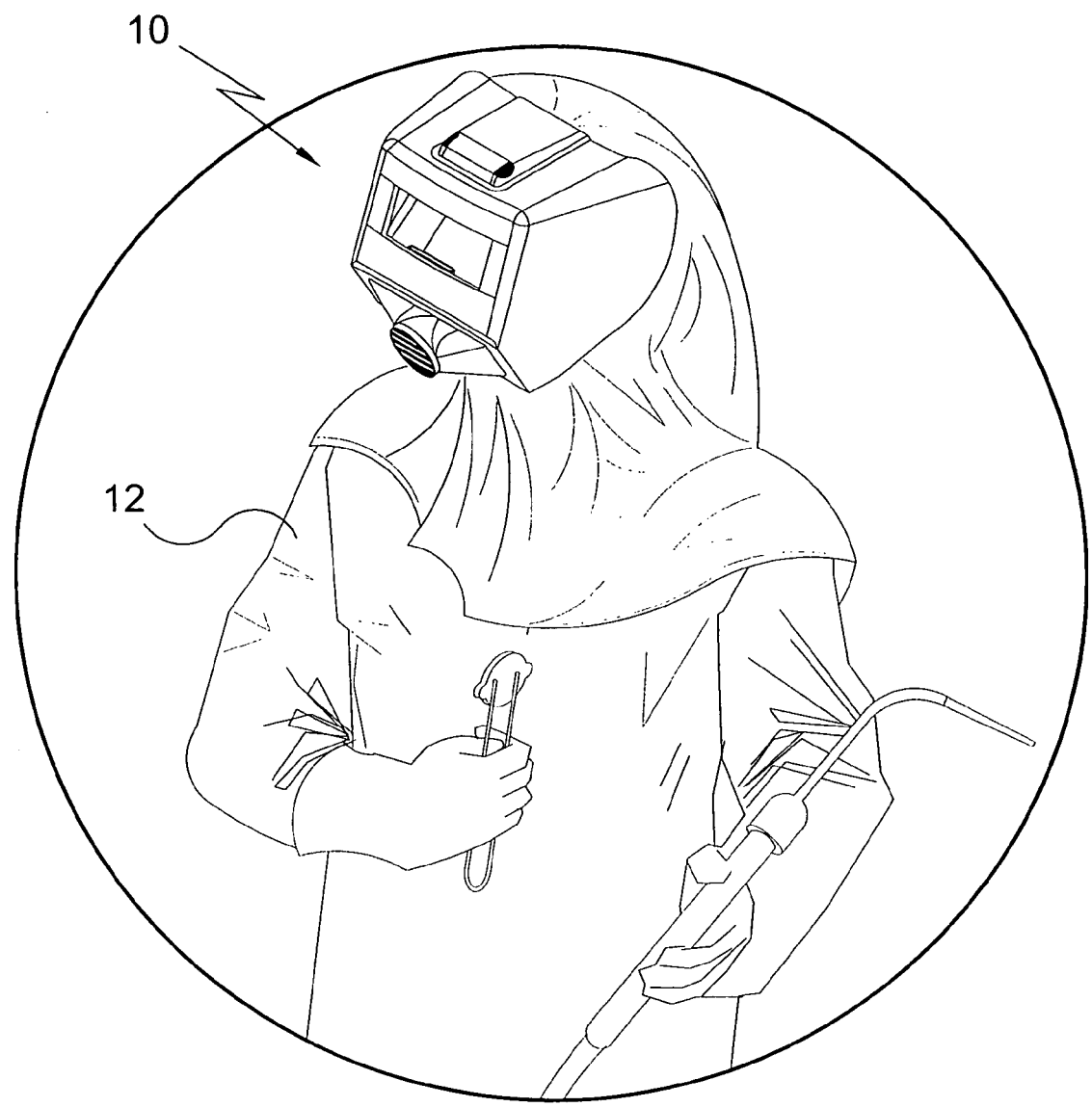
FIG. 1 is an illustrative view of the present invention in use.

With regard to reference numerals used, the following numbering is used throughout the drawings.

10 present invention
12 welder/user
14 fan
16 lens
18 power source
20 receptacle
22 filters
24 vents
26 lower nozzle
28 blower exhaust vent
30 lights
32 photovoltaic elements
34 inlet
36 outlet
38 outlet

DETAILED DESCRIPTION OF THE PREFERRED EMBODIMENT

The following discussion describes in detail one embodiment of the invention (and several variations of that embodiment). This discussion should not be construed, however, as limiting the invention to those particular embodiments since practitioners skilled in the art will recognize numerous other embodiments as well. For a definition of the complete scope of the invention, the reader is directed to the appended claims.

Turning to FIG. 1, shown therein is an illustrative view of the present invention 10 in use. The present invention 10 discloses a safer, healthier welding helmet designed to blow excessive noxious fumes and smoke away from the welder 12, and provides a plurality of fans (inner and outer) performing various tasks. The device 10 will help a welder 12 by reducing the cost of medical problems associated with breathing noxious fumes while welding.

Figure 2:
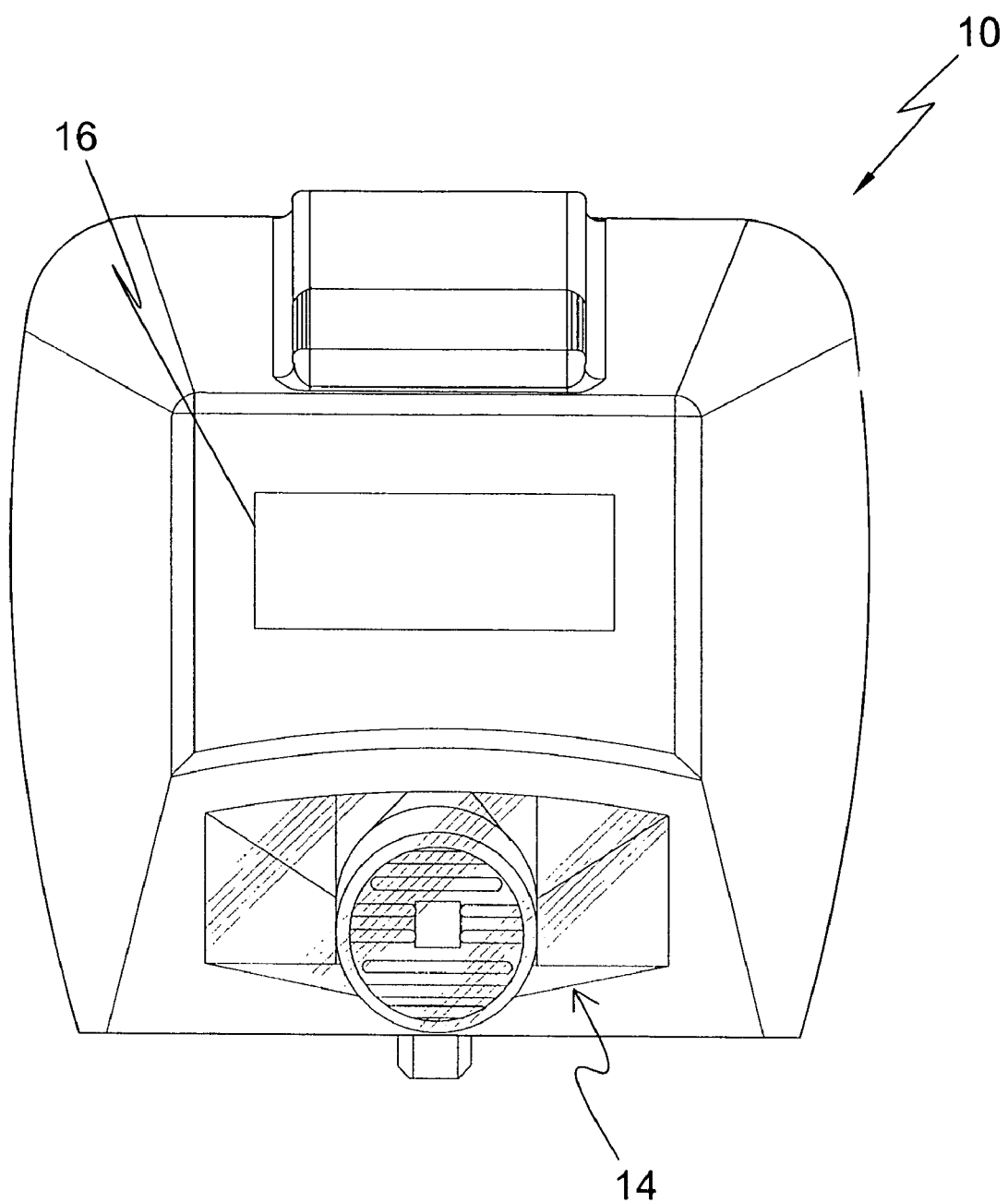
FIG. 2 is a frontal view of the present invention.

Turning to FIG. 2, shown therein is a frontal view of the present invention 10. Shown is the present invention 10 and the main component of the design fan 14. The fan 14 has a single or double blade with directionals to blow noxious gases, smoke and other cancer causing fumes away from the user. There are also inner vents to keep the lens 16 from fogging, cool the welder and keep noxious gases, smoke and fumes from entering the helmet from the rear area. The welding lens 16 is replaceable with clear or other color lens for other use such as sanding, painting, sand blasting, asbestos removal and more.

Figure 3:
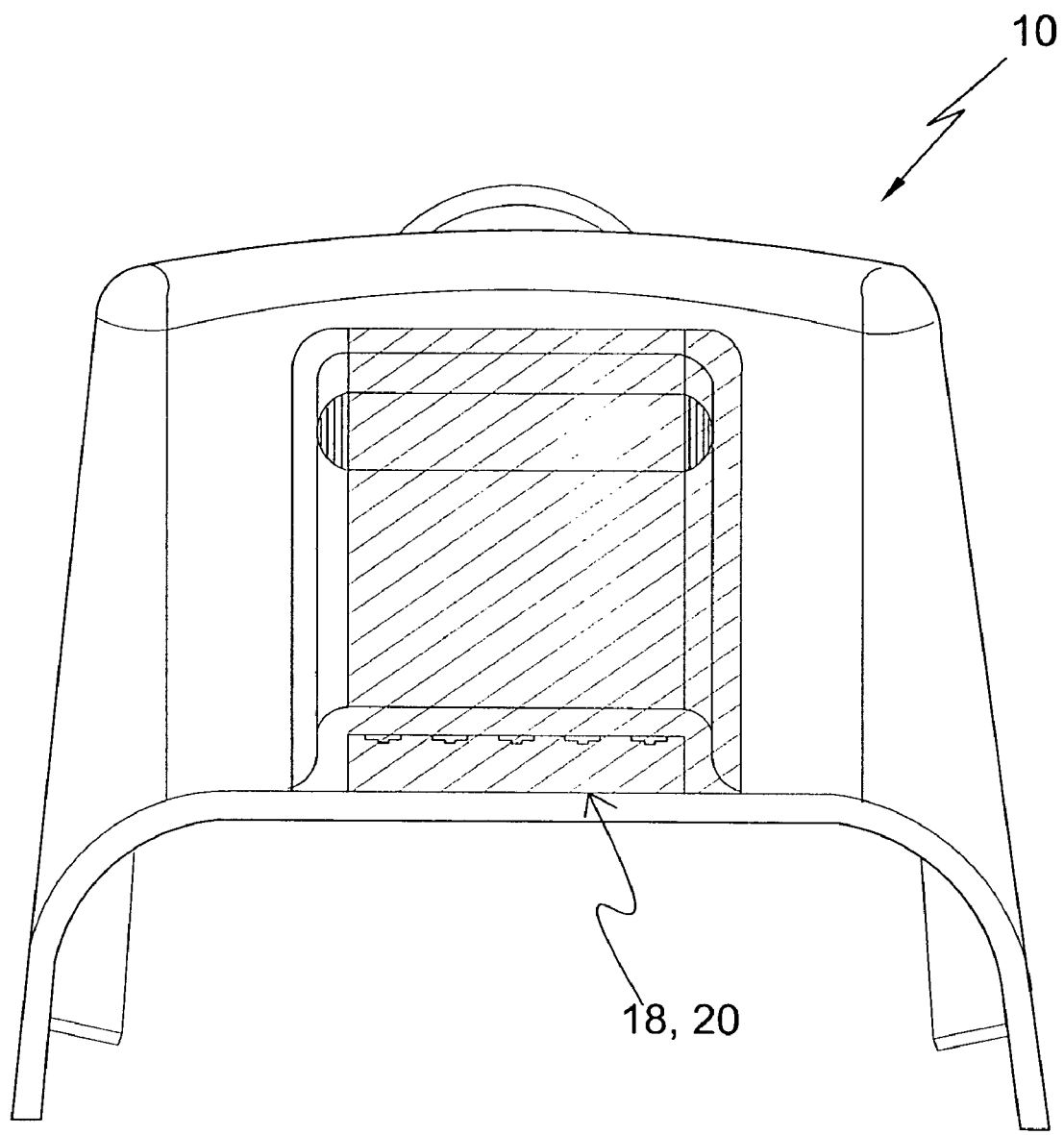
FIG. 3 is a view of the present invention.

Turning to FIG. 3, shown therein is a view of the present invention 10. Shown is the present invention 10. This view shows the cross section area of the suggested placement of the means for receiving and applying a potential 18 to the present invention 10 which can contain the power source. In this portion the user can slide a packet of lithium ion batteries into the receptacle 20. A plurality of batteries are recommended for a longer life use. The flash of the weld using light sensitive materials can recharge the batteries.

Figure 4:
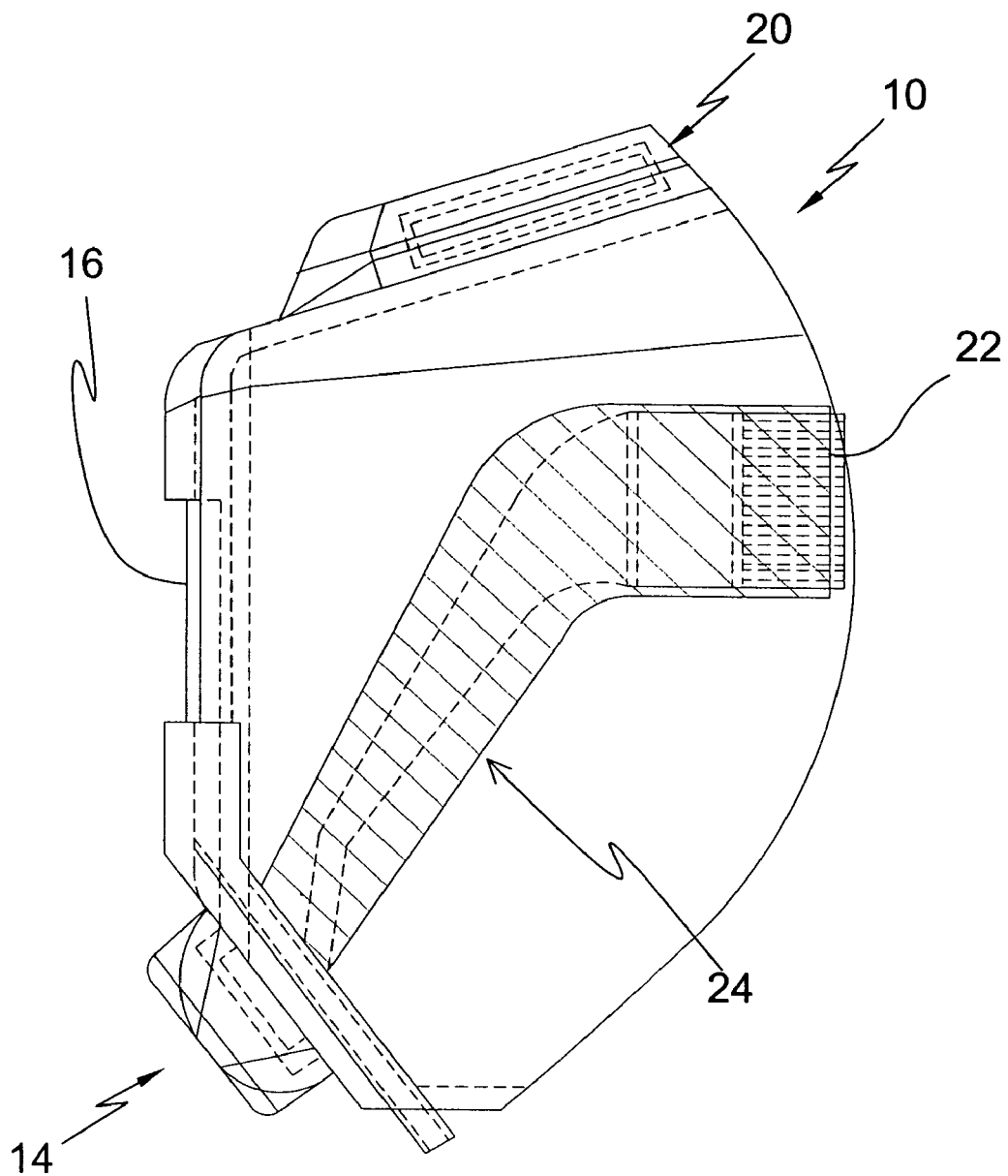
FIG. 4 is a side view of the present invention.

Turning to FIG. 4, shown therein is a side view of the present invention 10. This view shows a side view of the helmet of the present invention 10 with cross section of filters 22 and suction vents 24 and other features such as lens 16. Other previously disclosed elements are also shown.

Figure 5:
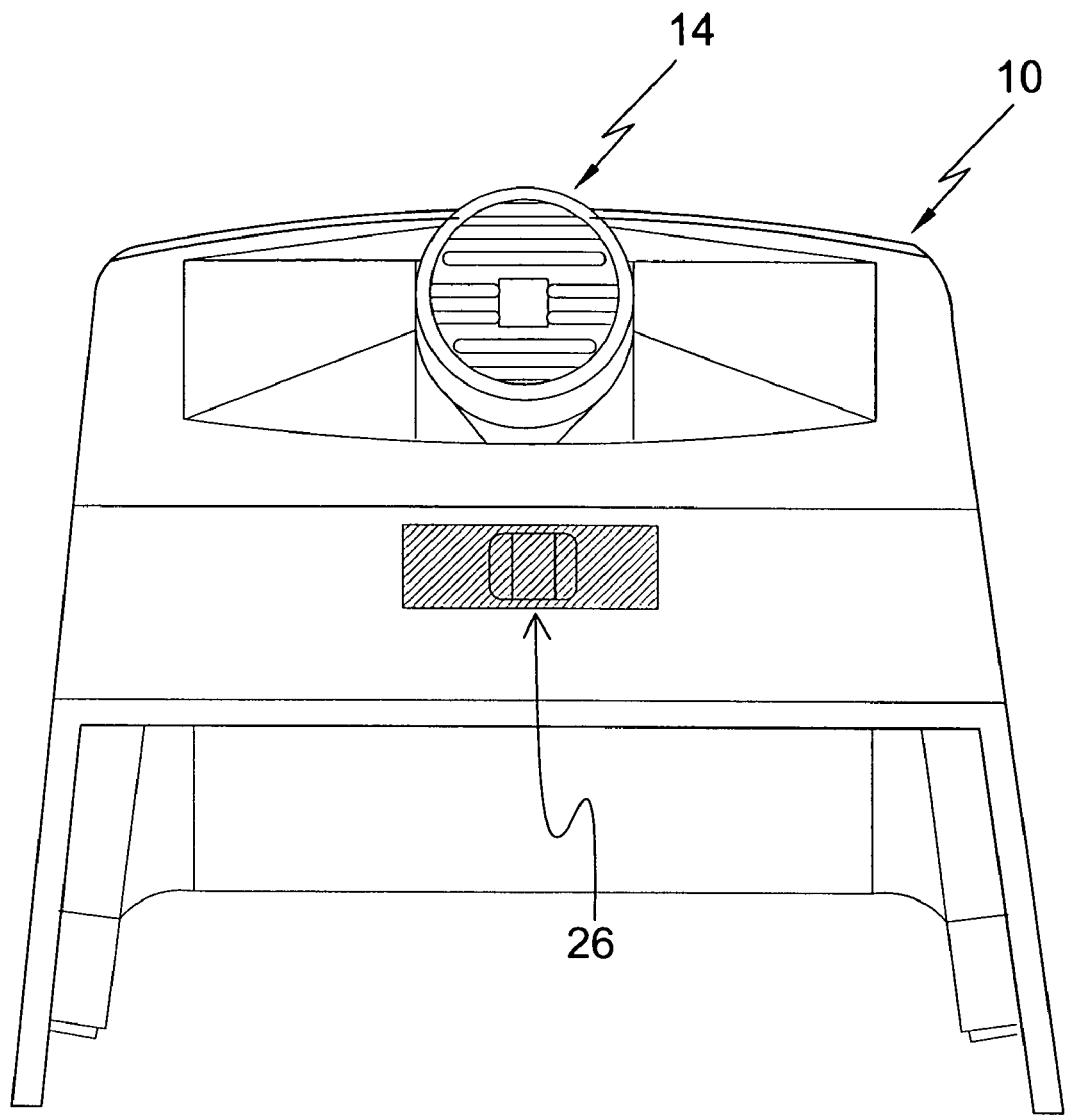
FIG. 5 is a view of the present invention.

Turning to FIG. 5, shown therein is a view of the present invention 10. This view represents the lower nozzle 26 which is as wide as the blower 14. The nozzle 26 is to hook accessory attachments, such as flat hoses in the front and rear of the user. They extend to the user's feet, if need be. This will cool the user's body in different weather conditions.

Figure 6:
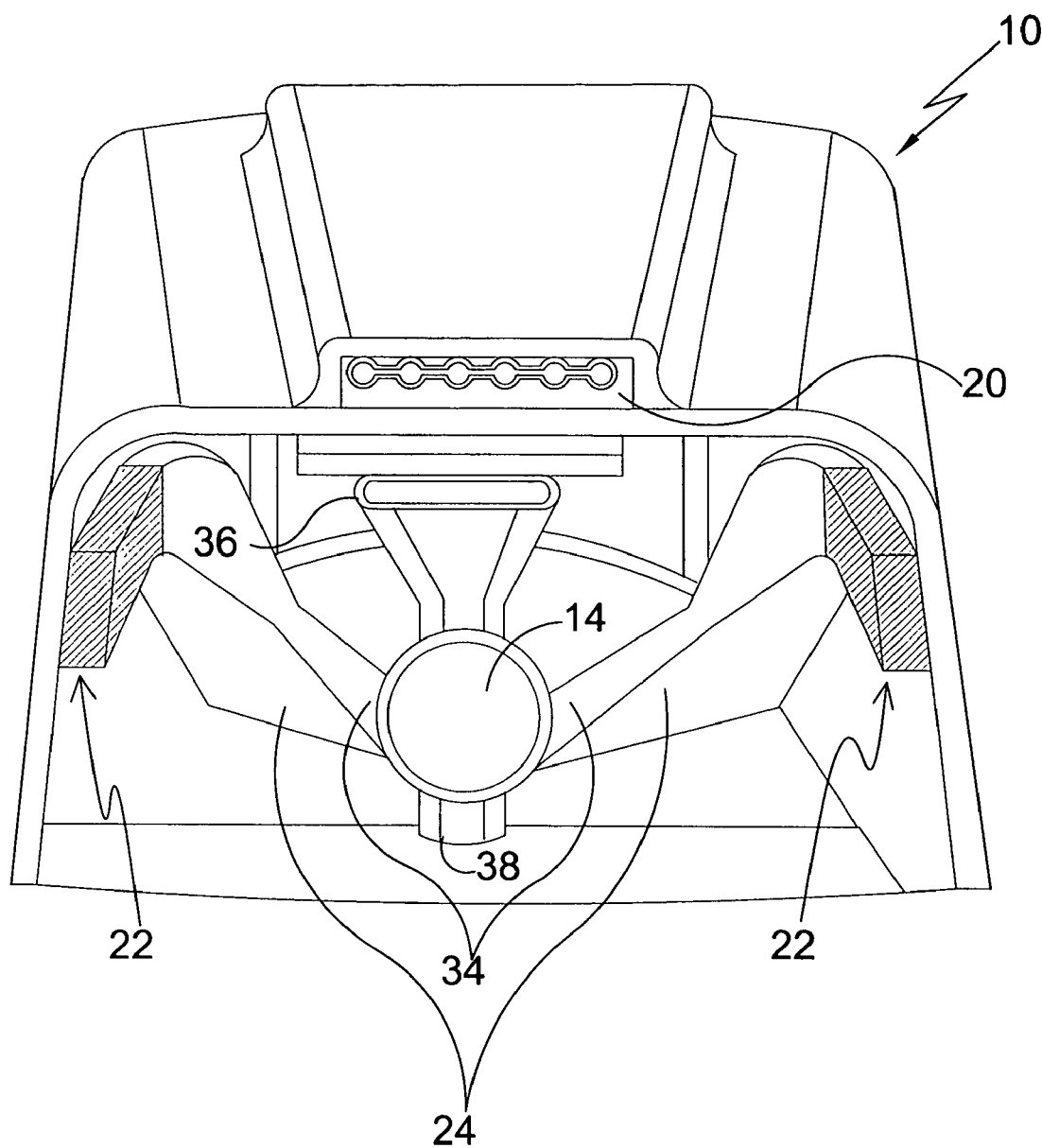
FIG. 6 is a view of the present invention.

Turning to FIG. 6, shown therein is a view of the present invention 10. This view represents the replaceable particle filter 22, HEPA filter or respirator elements that can be snapped into the suction vents to help eliminate the use of in-helmet cumbersome respirators. Also shown are the inlet 34 to the fan 14 and the first 36 and second 38 outlets from the fan along with the air ducts 24 and receptacle 20.

Figure 7:
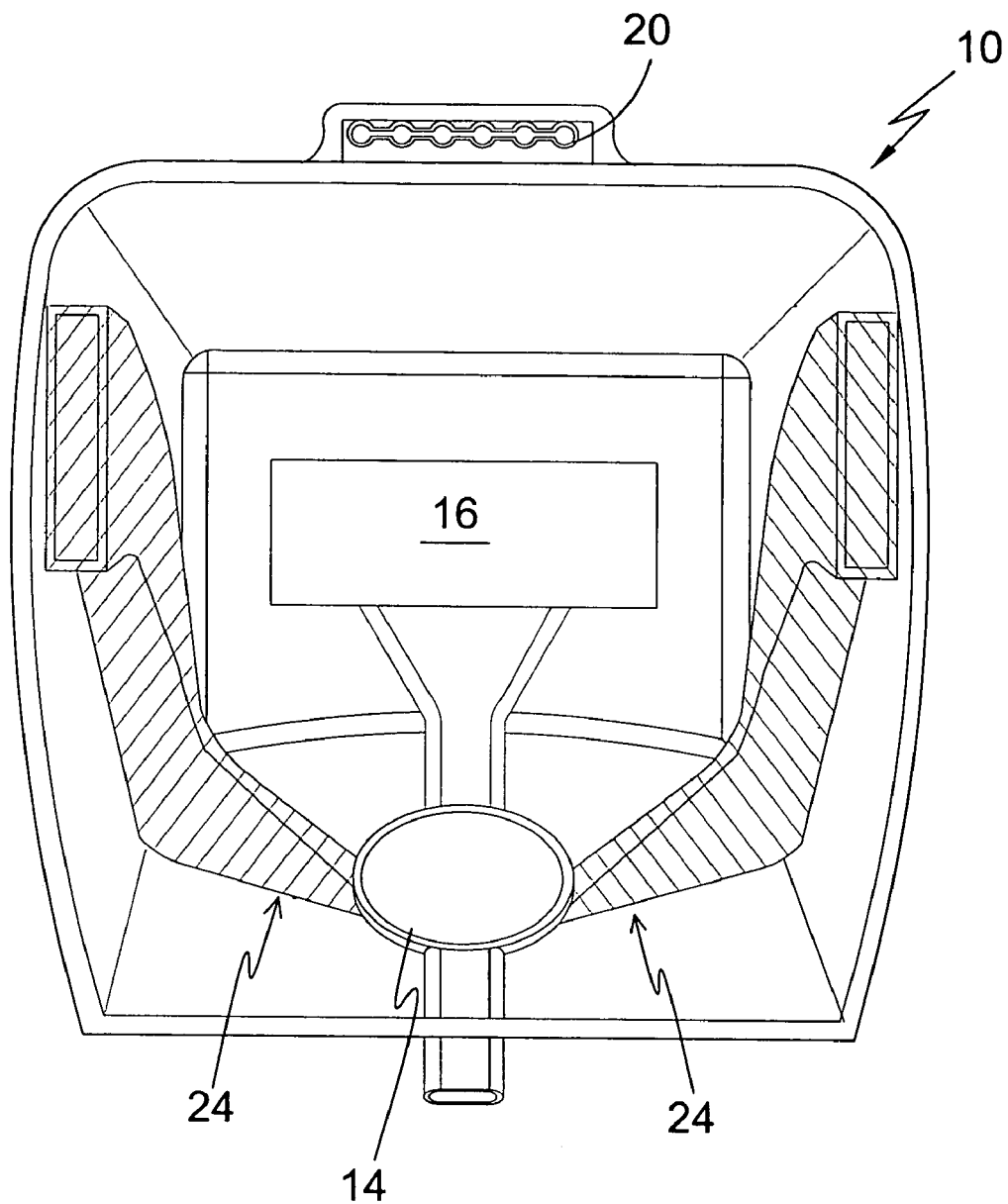
FIG. 7 is a view of the present invention.

Turning to FIG. 7, shown therein is a view of the present invention 10. This view represents the suction vents 24 that are attached to the blower 14. Also shown are lens 16 and receptacle 20.

Figure 8:
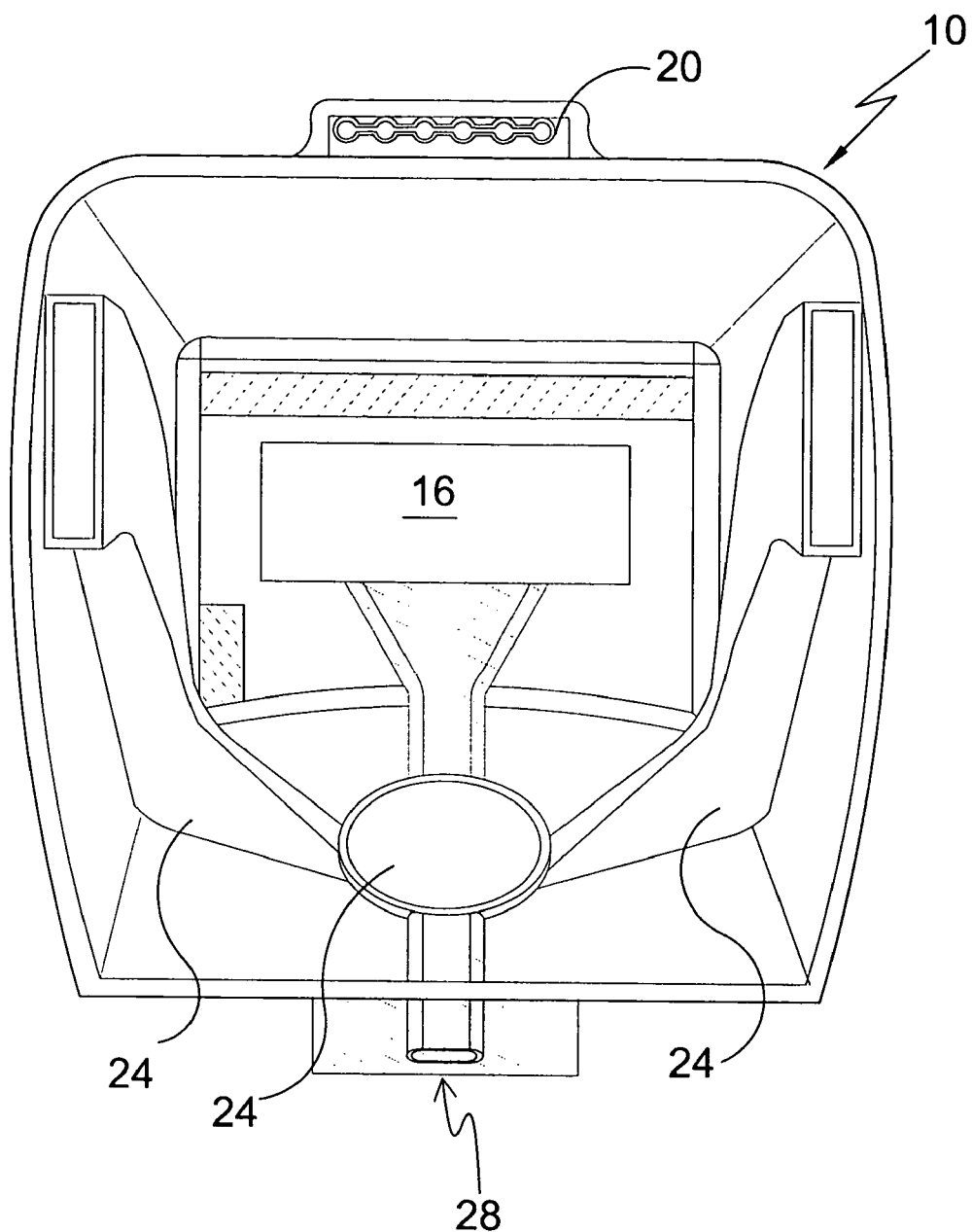
FIG. 8 is a view of the present invention.

Turning to FIG. 8, shown therein is a view of the present invention 10. This view shows the blower exhaust vents 28, these areas are suggested areas of placement for the added vents to prevent fogging, cool the user and prevent rear entry of gases, smoke and fumes. Other previously disclosed elements are also shown.

Figure 9:
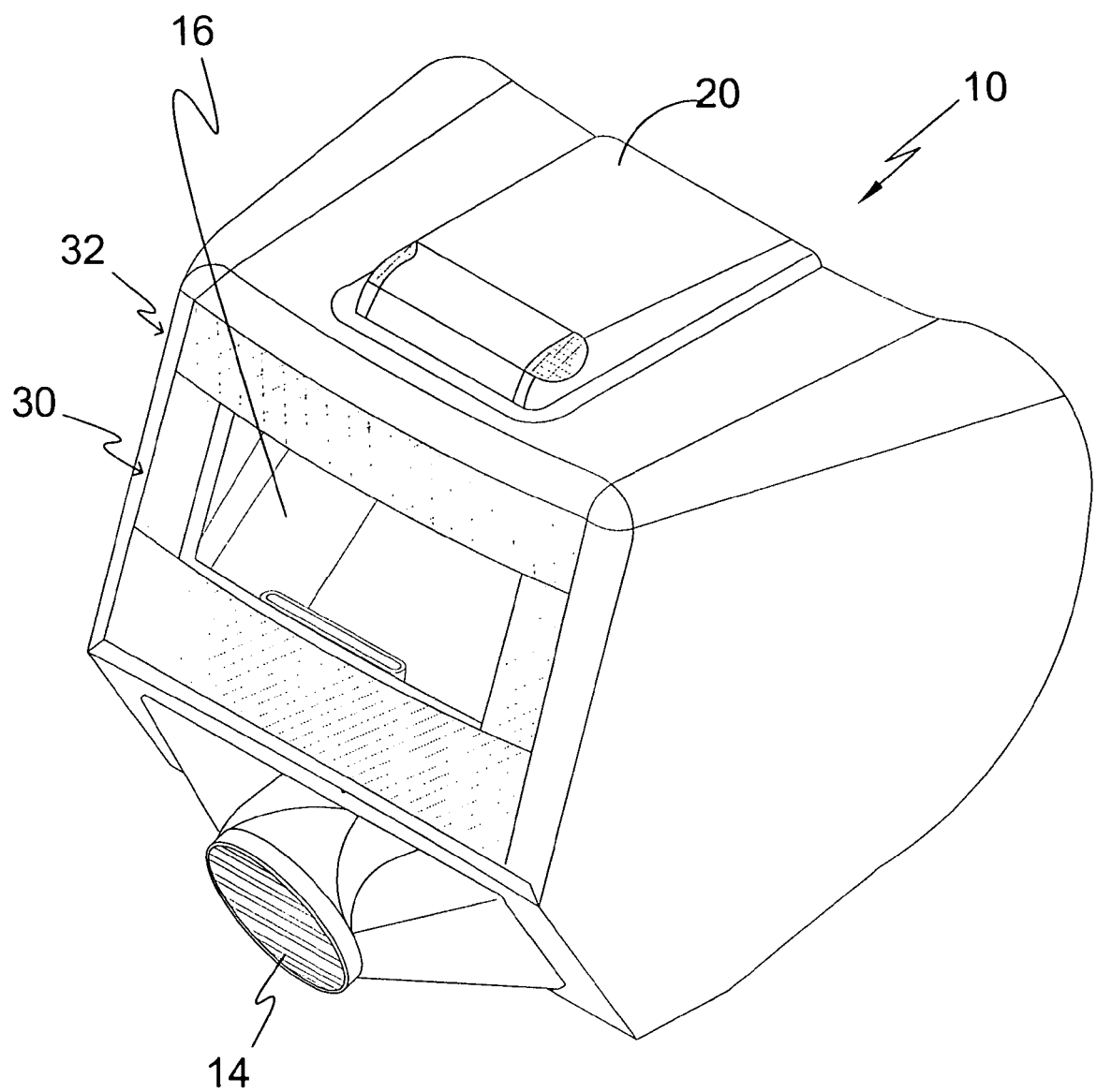
FIG. 9 is a perspective view of the present invention.

Turning to FIG. 9, shown therein is a perspective view of the present invention 10. In this view the cross section areas are bright lights 30 molded into the helmet for a better view of the work being done when welding. The double cross section represents the area where the light sensitive photovoltaic materials 32 can be placed to recharge the power sources contained in receptacle 20. The welding lens 16 is replaceable with other lens allowing the device to be used for other tasks. Also shown is fan 14.

What is claimed to be new and desired to be protected by Letters Patent is set forth in the appended claims.

I claim:

1. An apparatus for a self-contained welding helmet, comprising:
   a) a helmet for being mounted on the head of a user, said helmet having a front wall having upper and lower portions, a pair of laterally spaced side walls and a top extending rearwardly from said front wall defining an interior space adapted to receive the head of a user therein, said side walls having a rear end;
   b) a lens being disposed on said front wall of said helmet so that a user can see through said lens, wherein said lens can be removed from said wall and replaced in said wall;
   c) a fan having an electrical drive motor thereon being disposed on said front wall of said helmet for directing airflow about said helmet, said fan having an air inlet port and first and second air exhaust ports;
   d) a plurality of air ducts having first and second ends being disposed on said interior of said helmet so that said first end is connected to said air inlet port of said fan and said second end is disposed on each said side wall proximate said rear end of said side wall so that air enters said second end of said air duct wherein the air is drawn toward said fan;
   e) an air filter being disposed on said second end of each said air duct so as to filter the air being drawn toward said fan;
   f) wherein said first air exhaust port is adapted to blow air across said lens so that said lens is kept free of condensation;
   g) wherein said second air exhaust port is adapted to blow air downwardly from said front wall of said helmet, said second air exhaust port having an end thereon;
   h) a plurality of lights being disposed on said front wall so that a workspace can be lighted;
   i) means for receiving and applying a potential to said electrical drive motor and said lights whereby the electrical drive motor and lights can be energized;
   j) a plurality of photovoltaic elements being disposed on said front wall of said helmet so as to be energized by the flash of a weld, wherein said photovoltaic elements can recharge a battery; and,
   k) wherein said plurality of photovoltaic elements is in electrical communication with said means for receiving and applying a potential.

2. The apparatus of claim 1, wherein said means for receiving and applying a potential comprises a receptacle for receiving a battery, a battery being disposed in said receptacle, wherein said photovoltaic elements are electrically connected to said battery so as to recharge said battery as said photovoltaic elements are energized by the flash of a weld.

3. The apparatus of claim 2, wherein said battery comprises a lithium ion battery.

4. The apparatus of claim 3, wherein said receptacle is disposed on said top of said helmet.

5. The apparatus of claim 4, wherein said second air exhaust port is disposed on said lower portion of said front wall.

6. The apparatus of claim 5, wherein said second air exhaust port has the same width as said fan.

7. The apparatus of claim 6, wherein said end of said second air exhaust port is adapted to have a hose attached thereto so that air can be conveyed through said hose toward a user to permit a user to be cooled.

8. The apparatus of claim 7, wherein said lens comprise different colors so that a first lens having a first color can be removed and replaced with a second lens having a second color.

9. The apparatus of claim 8, further comprising a plurality of fans, wherein said plurality of fans comprise a fan disposed on said interior of said helmet and a fan disposed on the exterior of said helmet.

10. The apparatus of claim 9, wherein said filter is a filter for particulate matter.

11. The apparatus of claim 10, wherein said filter is a HEPA filter.

* * * * *